United States Patent
Oku

(10) Patent No.: US 9,743,826 B2
(45) Date of Patent: Aug. 29, 2017

(54) ENDOSCOPIC INSERTION SECTION TIP AND ENDOSCOPE

(75) Inventor: Masatoshi Oku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 1115 days.

(21) Appl. No.: 13/592,063

(22) Filed: Aug. 22, 2012

(65) Prior Publication Data
US 2013/0060083 A1 Mar. 7, 2013

(30) Foreign Application Priority Data

Sep. 5, 2011 (JP) ................................ 2011-192392

(51) Int. Cl.
*A61B 1/00* (2006.01)
*A61B 1/018* (2006.01)

(52) U.S. Cl.
CPC .......... *A61B 1/0008* (2013.01); *A61B 1/0011* (2013.01); *A61B 1/018* (2013.01)

(58) Field of Classification Search
CPC .............. A61B 1/0008; A61B 18/1492; A61B 2018/00434
See application file for complete search history.

(56) References Cited

U.S. PATENT DOCUMENTS

| | | | | |
|---|---|---|---|---|
| 3,933,397 A | * | 1/1976 | Hood | A63C 17/22 301/5.7 |
| 6,888,308 B1 | * | 5/2005 | Guenther | H01L 51/5237 313/504 |
| 2007/0118013 A1 | * | 5/2007 | Miyagi | A61B 1/00096 600/129 |
| 2010/0152540 A1 | * | 6/2010 | Tanoue | G02B 23/2492 600/175 |

FOREIGN PATENT DOCUMENTS

| | | | | |
|---|---|---|---|---|
| JP | 2006-320543 A | | 11/2006 | |
| JP | 2012120635 A | * | 6/2012 | ............... A61B 1/00 |

OTHER PUBLICATIONS

Extended European Search Report dated Oct. 8, 2012.

* cited by examiner

*Primary Examiner* — John P Leubecker
*Assistant Examiner* — Rajaa El Alami
(74) *Attorney, Agent, or Firm* — McGinn IP Law Group, PLLC

(57) ABSTRACT

A tip of an endoscopic insertion section includes a tip body having a forceps hole, and a cap covering the distal face of the tip body and having an opening corresponding to the forceps hole. Protrusions are provided between the distal face of the tip body and the opposite face of the cap that is opposite to the distal face, so that a specified space is formed between the distal face and the opposite face with the protrusions. In the space, at least a region around the forceps hole is filled with an adhesive so as to adhere the tip body and the tip cap together with no voids in the adhesive surrounding the forceps hole and thereby prevent disadvantages due to the entrance of a body fluid or a chemical cleaning solution through such voids.

15 Claims, 4 Drawing Sheets

ENDOSCOPIC INSERTION SECTION TIP AND ENDOSCOPE

BACKGROUND OF THE INVENTION

The present invention relates to a tip of an endoscopic insertion section. Particularly, the present invention is drawn to an endoscopic insertion section tip, in which secure adhesion and sealing are attained between a tip body and a cap for covering the tip body, and an endoscope having such a tip.

As is well-known, an endoscope is a medical instrument inserted into the living body of a human being, for instance, for diagnosis or examination on organs.

An endoscope basically includes an insertion section to be inserted into a human body, an operating section for operating the endoscope by manipulating the insertion section, supplying air/water, and so forth, a connector (light guide (LG) connector) connected with a source of air, a suction pump, and the like, and a universal cord (LG flexible section) for connecting the connector with the operating section and the insertion section.

The insertion section has a tip, in which an imaging unit provided with a CCD sensor, an illumination lens, and the like are incorporated, an elongated flexible portion toward the proximal end of the section, and an angling portion between the tip and the flexible portion, with the angling portion being bent in accordance with an operation through the operating section of the endoscope.

In the tip of the insertion section, an imaging unit with a CCD sensor, a light guide (optical fiber) for light propagation, an illumination lens for illuminating the site to be examined with light propagated through the light guide, and the like are incorporated. In addition, such holes as a forceps hole (forceps channel) and an air supply hole (air supply channel) for air/water supply are opening into the tip.

FIG. 5 schematically shows a cross section of a tip of an endoscopic insertion section. As shown in FIG. 5, a tip 100 of an endoscopic insertion section generally includes a tip body 102 having such components as an imaging unit incorporated therein and a forceps hole 108 and the like formed therein, and a tip cap 104 in a nearly cylindrical shape for covering the distal end of the tip body 102. The tip body 102 is normally made of metal. In FIG. 5, a resin or rubber jacket for covering the whole insertion section except for the tip cap 104 is denoted by a reference character 106.

As mentioned above, the tip body 102 has the forceps hole 108 and the like formed therein. The forceps hole 108 consists of a through hole formed in the tip body 102 and a tube 108a with its distal end being inserted/fixed in the through hole. In the tip cap 104, an opening 110 corresponding to the forceps hole 108 is formed.

The tip body 102 and the tip cap 104 are fixed together normally by using an adhesive to adhere the distal face of the tip body 102 and the inner face (hereafter referred to as "opposite face") of the tip cap 104 that is opposite to the distal face of the tip body 102 to each other, as described in JP 2006-320543 A, for instance.

SUMMARY OF THE INVENTION

In general, the distal face of the tip body 102 and the opposite face of the tip cap 104 (adhesion faces of the tip body 102 and the tip cap 104) are both flat. The parallelism between the distal face of the tip body 102 and the opposite face of the tip cap 104 thus depends largely on the density of presence of the adhesive between the faces.

On the other hand, an adhesive is manually applied to the distal face of the tip body 102 or the opposite face of the tip cap 104 because, as is well-known, a tip of an endoscopic insertion section is minute in size. After the application of an adhesive, the tip cap 104 is set onto the tip body 102 also manually.

Such manual handling may cause the adhesive between the distal face of the tip body 102 and the opposite face of the tip cap 104 to vary in density of presence and give a tilt to the faces. Moreover, the tip cap 104 may be adhered to the tip body 102 in a tilted state.

If the tip body 102 and the tip cap 104 are adhered together under such conditions that the distal face of the tip body 102 and the opposite face of the tip cap 104 are not parallel to each other, the adhesive will unevenly be present between the adhesion faces in an adhered part on the periphery of the forceps hole 108 (and the opening 110). In other words, voids will be left in the adhesive at the adhesion faces around the forceps hole 108.

The forceps hole 108 is provided in order to insert various procedure devices such as a forceps and a clipping device to the site to be examined and, accordingly, communicates with the outside (that is to say, is equivalent to the outside on an endoscopic basis).

It is thinkable that a body fluid of a subject enters the forceps hole 108. During the cleaning of the endoscope, the forceps hole 108 is filled with a cleaning solution flowing through it.

Consequently, voids in the adhesive at the adhesion faces around the forceps hole 108 may permit bacteria into them, leading to risk of infection.

In addition, voids in the adhesive around the forceps hole 108 may permit a chemical solution into them during the cleaning of the endoscope, which reduces the adhesive in adhesion strength. The chemical solution having entered the voids in the adhesive may enlarge the voids. If the voids in the adhesive are enlarged, the chemical solution may further enter the light guide or the imaging unit through the voids to cause a breakdown and other troubles.

If the adhesive is deteriorated by the chemical solution to an undue extent, the tip cap 104 will come away from the tip body 102.

An object of the present invention is to solve the above problems with the prior art by forming a specified space with a uniform height between the distal face of a tip body and the opposite face of a tip cap (that is to say, between the adhesion faces) to thereby allow a region required to be sealed, such as the periphery of a forceps hole, to be filled with an adhesive at a reliable and uniform density of presence, so as to provide an endoscopic insertion section tip whose tip body and tip cap are able to be appropriately adhered to each other, with the sealing of the periphery of a forceps hole communicating with the outside, for instance, being secured with no voids in the adhesive around the hole, and an endoscope including an insertion section having such a tip.

In order to achieve the object as above, the present invention provides a tip of an endoscopic insertion section to be inserted into a body cavity, comprising: a tip body having a forceps hole; a cap for covering a distal face of the tip body, the cap having an opening corresponding to the forceps hole; protrusions provided between the distal face of the tip body and a face of the cap that is opposite to the distal face; and an adhesive with which a gap formed by the protrusions between the tip body and the cap is filled such that the adhesive at least surrounds a perimeter of the forceps hole of the tip body.

In the tip of an endoscopic insertion section according to the present invention, it is preferable that the protrusions are three in total number.

Further, it is preferable that the tip comprises one linear protrusion and another protrusion, with the protrusions being uniform in height of their tops.

Further, it is preferable that the distal face of the tip body and the face of the cap that is opposite to the distal face are kept parallel to each other by the protrusions.

Further, it is preferable that the forceps hole has an extension throughout its perimeter that projects from the distal face of the tip body to such an extent that the extension is smaller in height than the protrusions.

Further, it is preferable that the forceps hole includes a tubular member forming the forceps hole, and a distal end portion of the tubular member constitutes the extension.

Furthermore, it is preferable that the gap formed by the protrusions between the tip body and the cap is filled with the adhesive in its entirety.

The present invention also provides an endoscope including an insertion section to be inserted into a body cavity, which is adapted to inspect a site to be inspected by inserting the insertion section into the body cavity, wherein: a tip of the insertion section comprises a tip body having a forceps hole; a cap for covering a distal face of the tip body, the cap having an opening corresponding to the forceps hole; protrusions provided between the distal face of the tip body and a face of the cap that is opposite to the distal face; and an adhesive with which a gap formed by the protrusions between the tip body and the cap is filled such that the adhesive at least surrounds a perimeter of the forceps hole of the tip body.

In the endoscope according to the present invention, it is preferable that the protrusions of the tip are three in total number.

Further, it is preferable that the tip of the insertion section comprises one linear protrusion and another protrusion, with the protrusions being uniform in height of their tops.

Further, it is preferable that the distal face of the tip body and the face of the cap that is opposite to the distal face are kept parallel to each other by the protrusions of the tip of the insertion section.

Further, it is preferable that the forceps hole of the tip body has an extension throughout its perimeter that projects from the distal face of the tip body to such an extent that the extension is smaller in height than the protrusions.

Further, it is preferable that the forceps hole of the tip body includes a tubular member forming the forceps hole, and a distal end portion of the tubular member constitutes the extension.

Furthermore, it is preferable that the gap formed by the protrusions of the tip of the insertion section between the tip body and the cap is filled with the adhesive in its entirety.

According to the present invention with the configuration as above, in a tip of an endoscopic insertion section, the distal face of a tip body and the opposite face (face opposite to the distal face of the tip body) of a tip cap are kept parallel to each other by protrusions provided between the distal face and the opposite face (three protrusions formed on the distal face of the tip body, for instance).

In other words, in the endoscopic insertion section tip according to the present invention, a specified space with a uniform height is formed between the adhesion faces of the tip body and the tip cap by protrusions provided between the distal face of the tip body and the opposite face of the tip cap, and the tip body and the tip cap are adhered together by filling the space with an adhesive.

According to the present invention as above, the space between the distal face of the tip body and the opposite face of the tip cap (that is to say, between the adhesion faces) can be filled with an adhesive at a uniform density so as to adhere the tip body and the tip cap together, by applying the adhesive to the distal face of the tip body at a thickness exceeding the height of the protrusions, for instance.

Thus in the endoscopic insertion section tip of the invention, the tip body and the tip cap are adhered together with a secured sealing, with no voids being left in the adhesive around the forceps hole and the like, so that body fluids and chemical solutions are prevented from entering voids in the adhesive. As a result, risk of infection caused by voids in the adhesive around the forceps hole and the like, and faults due to the deterioration of the adhesive, such as the breakdown of the imaging unit and the coming away of the tip cap, are prevented with advantage.

Since the applied adhesive can have a larger thickness than usual owing to the protrusions, the deterioration of the adhesive by a chemical solution is further retarded.

In addition, the protrusions allow an adhesive to have a higher fluidity during the adhesion of the tip body and the tip cap to each other. In consequence, a wider region between the distal face of the tip body and the opposite face of the tip cap (or, between the adhesion faces) can be filled with the adhesive, which further improves the adhesion between the tip body and the tip cap.

DETAILED DESCRIPTION OF THE INVENTION

In the following, the endoscopic insertion section tip and the endoscope, both according to the present invention, are detailed in reference to the preferred embodiments as shown in the accompanying drawings.

Figure 1:
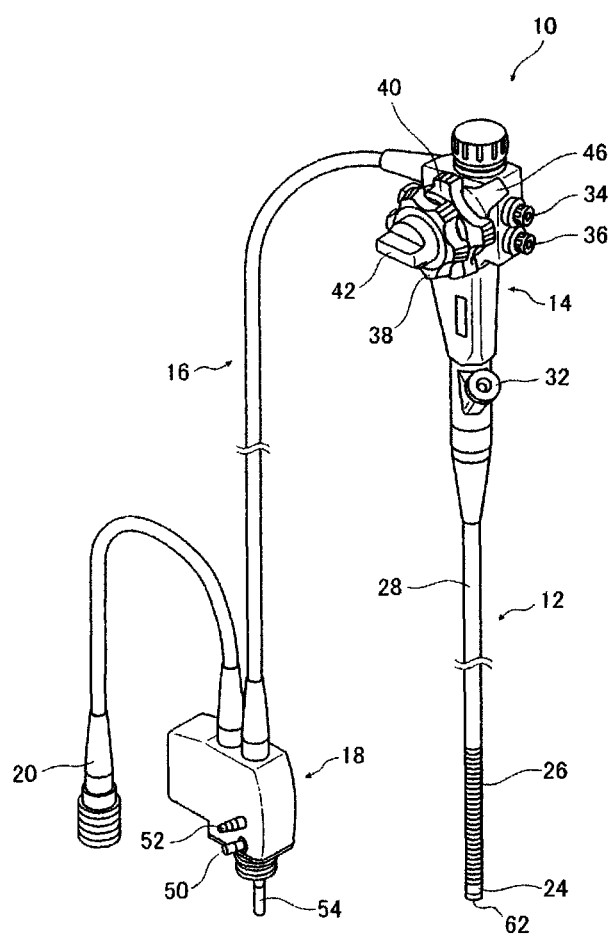
FIG. 1 is a diagram schematically showing an example of the endoscope of the present invention using the endoscopic insertion section tip of the present invention.

FIG. 1 schematically shows an example of the endoscope of the present invention using the endoscopic insertion section tip of the present invention.

An endoscope 10 shown in FIG. 1 is adapted to be inserted into the area where treatment or examination is to be conducted, such as a body cavity (e.g., alimentary canal, ear, nose, throat), so as to make an inspection, take a still image or a moving image, collect biological tissue, or perform other procedures in the living body.

The endoscope 10 is an endoscope of a so-called electronic type using a CCD sensor to image (or, take an image of) the site to be examined, so as to inspect the site or obtain a moving image or a still image of the site. Similar to the conventional endoscope, the endoscope 10 includes an insertion section 12, an operating section 14, a universal cord 16, a light guide (LG) connector 18, and a video connector 20.

The insertion section 12, as being an elongated section inserted to the site to be examined in a body cavity or the like, has a tip 24 at its distal end (insertion end, namely, end opposite to the end at which the operating section 14 is located), an angling portion 26, and a flexible portion 28, as is the case with a known endoscope.

The tip 24 is the endoscopic insertion section tip according to the present invention. The endoscope 10 is basically identical to a known endoscope except that the present invention is applied to the tip 24 of the insertion section 12.

The operating section 14 is a section for operating the endoscope 10.

Similar to the conventional endoscope, a forceps port 32 for inserting such a procedure device as a forceps that communicates with a forceps hole (forceps channel) 72, a suction button 34 for performing suction from the tip 24 using the forceps hole 72, an air/water supply button 36 for supplying air or water from the tip 24 to the site to be examined or the like using an air/water supply hole (air/water supply channel) 74, and the like are arranged in the operating section 14. Apart from the above, the endoscope 10, as being of an electronic type, is provided with various switches for inspecting/imaging the site to be examined with an imaging unit (CCD sensor), such as a zoom switch, a still image taking switch, a moving image taking switch, and a freeze switch.

In the operating section 14, an LR knob 38 for bending the angling portion 26 rightward/leftward, a UD knob 40 for bending the angling portion 26 upward/downward, as well as an LR brake 42 and a UD brake 46 for keeping the angling portion 26 in a bent state are also arranged.

The LG connector 18 is a component for connecting the endoscope 10 with a water supply means, an air supply means, a suction means, and the like in the facilities where the endoscope 10 is to be employed. The LG connector 18 has a water supply connector 50 for connecting the endoscope 10 with the water supply (water feeding) means in the facilities, a ventilation connector 52 for the connection with the air supply means, a suction connector for the connection with the suction means, a crimped terminal connected with an air feeding means, and the like arranged thereon.

The LG connector 18 also has an LG rod 54 for the connection with an illumination light source, and an S terminal used for connecting an S cord upon use of an electronic knife.

Since the endoscope 10 is an electronic endoscope, the LG connector 18 is connected with the video connector 20 for connecting the endoscope 10 with a processing unit. The image (image data) as obtained by the CCD sensor of the tip 24, and various instructions given through the operating section 14 are transmitted by a signal line via the LG connector 18 and outputted from the video connector 20 to the processing unit.

The universal cord (LG flexible section) 16 is a section connecting between the LG connector 18 and the operating section 14.

In the universal cord 16, a water supply channel connected with the water supply connector 50, an air supply channel connected with the ventilation connector 52, a suction channel connected with the suction connector, a light guide, a signal line, and the like are contained/inserted.

As mentioned before, the insertion section 12 of the endoscope 10 has the tip 24, the angling portion 26, and the flexible portion 28.

The angling portion (bending portion) 26 is a portion bendable upward/downward and rightward/leftward (that is to say, in four directions orthogonal to one another) in order to insert the tip 24 to a target location or position it at the target location. The angling portion 26 is bent by actuating the LR knob 38 and the like of the operating section 14.

The flexible portion 28 is an elongated portion linking the tip 24 and the angling portion 26 with the operating section 14. The flexible portion 28 has a length and flexibility adequate to the insertion to the site to be examined.

In the flexible portion 28 and the angling portion 26, the forceps hole 72 (a tube 72a described later), the air/water supply hole 74, the signal line which transmits an output signal from an imaging unit 68 of the tip 24, the light guide through which light is propagated to an illumination lens 70 of the tip 24, a wire for bending the angling portion 26, and the like are inserted.

Figure 2A:
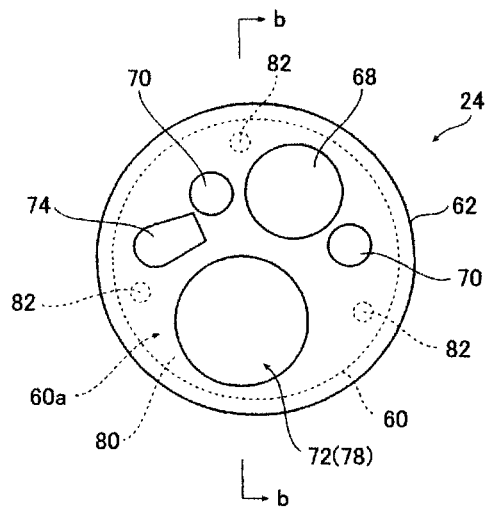
FIG. 2 schematically shows the tip of the insertion section of the endoscope as shown in FIG. 1, with FIG. 2A being a front view, and FIG. 2B a cross-sectional view, of the tip.
Figure 2B:
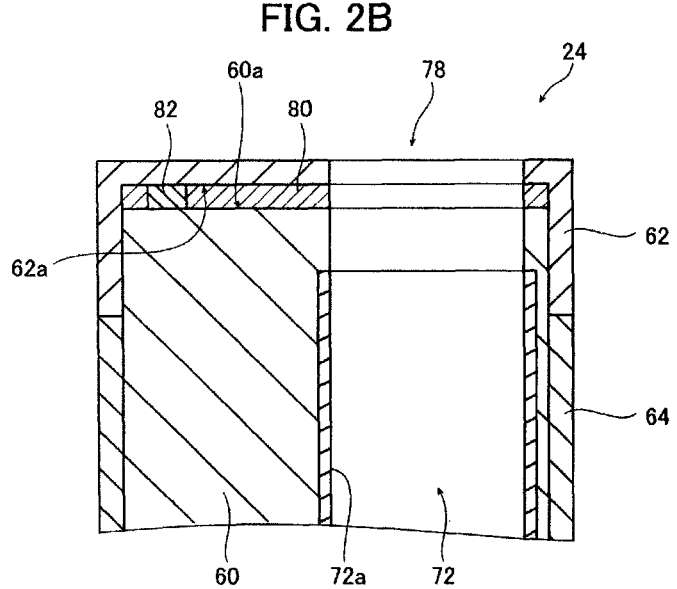

In FIG. 2A, the front face of the tip 24 (the distal face of the insertion section 12) is schematically shown. FIG. 2B is a schematic diagram showing the cross section along line b-b in FIG. 2A.

The tip 24 is comprised of a tip body 60, and a tip cap 62 in a nearly cylindrical shape for covering the distal end of the tip body 60. As an example, the tip body 60 is made of metal and the tip cap 62 is made of such a resin as polysulfone.

In FIG. 2B, a resin or rubber jacket for covering the whole insertion section 12 except for the tip cap 62 is denoted by a reference character 64.

In the endoscope 10 as shown, the imaging unit 68 and the illumination lens 70 (as well as a light guide) are incorporated in the tip body 60. In addition, the forceps hole 72 communicating with the forceps port 32, the air/water supply hole 74 for supplying air and water, and the like are formed in the tip body 60.

The imaging unit 68 has elements and optical components necessary for imaging, such as a CCD sensor and an imaging lens, integrated with one another into a unit. A signal line for transmitting the images as taken with the imaging unit 68 is inserted in the insertion section 12 (the angling portion 26 and the flexible portion 28), the operating section 14, the universal cord 16 and the LG connector 18, thus extending to the video connector 20.

The illumination lens 70 is a lens for illuminating the site to be examined with the light as propagated through a light guide (bundle of thin optical fibers, for instance). The tip body 60 is provided with a through hole for receiving the light guide, and the illumination lens 70 is positioned at the distal end of the through hole. The light guide is inserted in the insertion section 12, the operating section 14 and the universal cord 16, thus extending to the LG rod 54 of the LG connector 18.

The forceps hole 72 for inserting such a procedure device as a forceps to the site to be examined consists of a through hole formed in the tip body 60 and the tube 72a with its distal end being inserted/fixed in the through hole. The tube 72a, as extending through the insertion section 12, communicates with the forceps port 32 as mentioned above.

The air/water supply hole 74 also consists of a through hole formed in the tip body 60 and a tube (not shown) connected to the tip body 60. The tube constituting the air/water supply hole 74 is inserted in the insertion section 12, the operating section 14 and the universal cord 16, thus extending to the LG connector 18.

In the tip 24 of the endoscope 10, the tip cap 62 is so fixed to the tip body 60 as to cover a distal face 60a of the tip body 60.

The tip cap 62 has a nearly cylindrical shape, with its one end being opened, and is as such put over the distal end of the tip body 60. In the part of the tip cap 62 that faces the distal face 60a (so to speak, the ceiling of a cylinder), not only an opening 78 corresponding to the forceps hole 72 but openings corresponding to the imaging unit 68 and the illumination lens 70 provided on the tip body 60 and an opening corresponding to the air/water supply hole 74 are formed.

In the tip 24, the tip cap 62 is fixed to the tip body 60 by adhering the distal face 60a of the tip body 60 and the face (ceiling face) of the tip cap 62 which is opposite to the distal face 60a, namely an opposite face 62a to each other with an adhesive 80.

If necessary, the lateral face of the tip body 60 and the inner peripheral face of the tip cap 62 may be adhered together with an adhesive.

On the distal face 60a of the tip body 60, three protrusions 82 are formed.

In the tip 24 as shown, the part of the distal face 60a of the tip body 60 where neither a component is provided nor a hole, such as the forceps hole 72, is formed is flat. The part of the opposite face 62a of the tip cap 62 where an opening, such as the opening 78, is not formed is also flat. The flat parts serve as adhesion faces of the tip body 60 and the tip cap 62.

The protrusions 82 are equal in height. Consequently, the distal face 60a and the opposite face 62a as adhesion faces are kept parallel to each other by the protrusions 82.

In the endoscopic insertion section tip 24 of the present invention, the protrusions 82 which define a plane are provided between the distal face 60a of the tip body 60 and the opposite face 62a of the tip cap 62 so as to keep the distal face 60a and the opposite face 62a (adhesion faces of the tip body 60 and the tip cap 62) parallel to each other with the protrusions 82 and thus form a specified space with a uniform height between the two faces (adhesion faces).

The space as such is filled with an adhesive at a reliable and uniform density of presence, so that it is favorably possible to prevent voids in the adhesive from occurring in a region required to be sealed at the adhesion faces of the tip body 60 and the tip cap 62, such as the periphery of the forceps hole 72.

Figure 5:
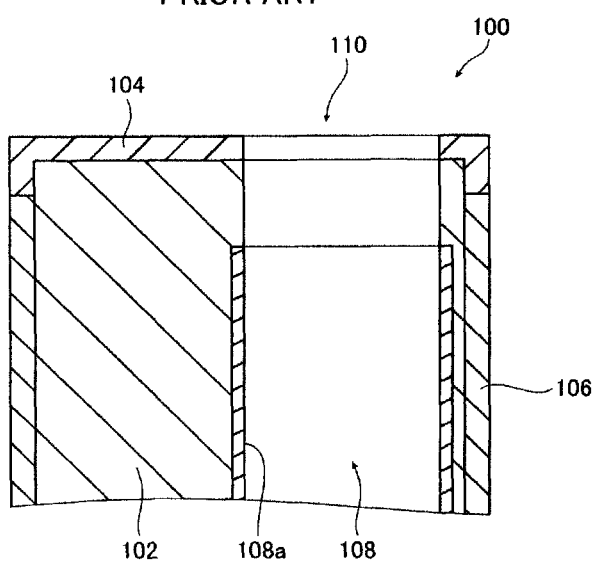
FIG. 5 is a diagram schematically showing a cross section of a conventional tip of an endoscopic insertion section.

As described before, in such a conventional tip of an endoscopic insertion section as shown in FIG. 5, the parallelism between the distal face of the tip body 102 and the opposite face of the tip cap 104 depends largely on the density of presence of an adhesive between the faces that may vary with location. Moreover, very delicate works, such as application of an adhesive onto the distal face of the tip body 102 or the opposite face of the tip cap 104 and setting of the tip cap 104 onto the tip body 102, are done by hand.

Consequently, it is often in a conventional tip of an endoscopic insertion section that the tip cap 104 is set onto the tip body 102 and adhered to it under such conditions that the distal face of the tip body 102 and the opposite face of the tip cap 104 are not parallel to each other. In that case, on the periphery of the forceps hole 108 and the like, the adhesive will unevenly be present between the distal face and the opposite face as adhesion faces, that is to say, voids will be left in the adhesive at the adhesion faces. Voids in the adhesive may permit a body fluid into them, leading to risk of infection. A chemical solution for endoscope cleaning having further entered through the voids in the adhesive may cause such troubles as the breakdown of an imaging unit, or the coming away of the tip cap.

In contrast, in the endoscopic insertion section tip of the present invention, the tip body 60 and the tip cap 62 are adhered together under such conditions that the distal face 60a and the opposite face 62a as adhesion faces are kept parallel to each other by providing three protrusions 82 between the distal face 60a and the opposite face 62a, as in the shown embodiment for instance.

In other words, according to the present invention, the distal face 60a and the opposite face 62a are kept parallel to each other and a specified space with a uniform height is formed between the faces 60a and 62a by providing the protrusions 82, which makes it possible to reliably fill the region between the adhesion faces that is required to be sealed, such as the periphery of the forceps hole 72, with an adhesive at an even and uniform density of presence (filling density) so as to carry out the adhesion of the tip body 60 and the tip cap 62 to each other.

Thus according to the present invention, the tip body 60 and the tip cap 62 can be adhered together with a secured sealing, with no voids being left in the adhesive at the adhesion faces around the forceps hole 72 and the like, so that body fluids and chemical solutions are prevented from entering voids in the adhesive. As a result, risk of infection caused by such voids as above, deterioration of the adhesive by a chemical solution having entered the voids, the entrance of a chemical solution into the imaging unit and so forth and the occurrence of troubles that are induced by a spread deterioration of the adhesive, coming away of the tip cap, and other problems are prevented with advantage.

In the conventional structure, a tip body and a tip cap (the distal face of the tip body and the opposite face of the tip cap) are adhered together by pressing them against each other, so that the thickness of the adhesive is not more than 30 μm. In the present invention, the adhesive 80 (in layer form) is allowed to have a larger thickness than usual by providing the protrusions 82, and the deterioration of the adhesive by a chemical solution, for instance, is retarded accordingly.

In addition, the protrusions 82 allow the adhesive 80 to have a higher fluidity between the distal face 60a and the opposite face 62a during the adhesion of the tip body 60 and the tip cap 62 to each other. In consequence, a wider region between the distal face 60a and the opposite face 62a can be filled with the adhesive, which further improves the adhesion between the tip body 60 and the tip cap 62.

In the endoscopic insertion section tip 24 of the present invention, it is basically acceptable that a gap formed by the protrusions 82 between the distal face 60a of the tip body 60 and the opposite face 62a of the tip cap 62 is filled with the adhesive 80 such that the adhesive 80 surrounds the perimeters of holes (openings) equivalent to the outside of the insertion section 12, such as the forceps hole 72, as long as an adequate adhesion is secured between the tip body 60 and the tip cap 62.

In other words, the tip body 60 and the tip cap 62 may be adhered together by applying the adhesive only to a region surrounding the perimeter of a hole or opening as a possible inlet for a chemical solution and so forth, such as the periphery of the opening 78 in the opposite face 62a of the tip cap 62 (and/or the periphery of the forceps hole 72 in the distal face 60a of the tip body 60), at a thickness exceeding the height of the protrusions 82.

It, however, is preferable that the entire region between the flat parts of the distal face 60a and the opposite face 62a is filled with the adhesive 80. Such a configuration allows a reliable adhesion of the tip body 60 and the tip cap 62 to each other, and a longer-term prevention of disadvantages due to the entrance of a chemical solution through voids in the adhesive 80.

For instance, it is preferable that the adhesive is applied to the whole of the opposite face 62a of the tip cap 62 (and/or the entire part to be adhered of the distal face 60a) at a thickness exceeding the height of the protrusions 82, and the tip body 60 and the tip cap 62 are adhered to each other such that the adhesive overflows into the forceps hole 72. The adhesive having overflowed into the forceps hole 72 and the like may be removed by a known method suitable for the adhesive in question, and so forth.

It is desirable in any case that the adhesive 80 is applied between the distal face 60a of the tip body 60 and the opposite face 62a of the tip cap 62 in a uniformly flat manner with no height variations with respect to the forceps hole 72, the opening 78, and the like equivalent to the outside of the endoscope 10.

In the present invention, no limitation is imposed on the adhesive 80 used to adhere the tip body 60 and the tip cap 62 together. Any known adhesive used in an endoscope to adhere a tip body and a tip cap together, such as an epoxy adhesive, is available.

The protrusions 82 are not limited in height but may have a height specified appropriately to the type of the endoscope 10, the size of the tip 24, and so forth.

According to studies by the present inventor, a preferred height of the protrusions 82 is 30 to 100 μm. A height of the protrusions 82 falling within such range yields favorable results in terms of the parallelism between the distal face 60a and the opposite face 62a, the fluidity (availability for filling) of the adhesive 80, the adhesion strength, and so forth.

The protrusions 82 are not limited in number to three (three point) as in the shown embodiment, either. Various structures are available to the present invention as long as the distal face 60a and the opposite face 62a are kept parallel to each other by a plurality of protrusions defining a plane.

Figure 3:
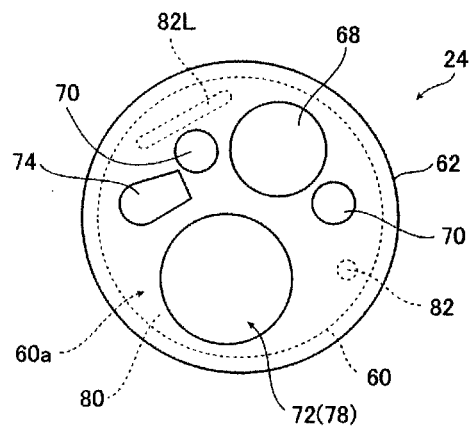
FIG. 3 is a diagram schematically showing the front face of another example of the endoscopic insertion section tip of the present invention.

For instance, a combination of one linear (longitudinal) protrusion 82L and one punctiform protrusion 82 schematically shown in FIG. 3, with their top faces being uniform in height, may define a plane and keep the distal face 60a and the opposite face 62a parallel to each other.

The protrusions 82 (82L) are not limitedly formed on the distal face 60a of the tip body 60.

The protrusions 82 may be formed on the opposite face 62a of the tip cap 62 or, alternatively, on both the distal face 60a of the tip body 60 and the opposite face 62a of the tip cap 62. If the three protrusions 82 as shown in FIG. 2 are to be used, for instance, it is also possible to form two protrusions on the distal face 60a and one on the opposite face 62a.

In each of the endoscopic insertion section tips as shown in FIGS. 2 and 3, the tube 72a forming the forceps hole 72 does not reach the distal end of the tip body 60, to which the present invention is not limited.

Figure 4:
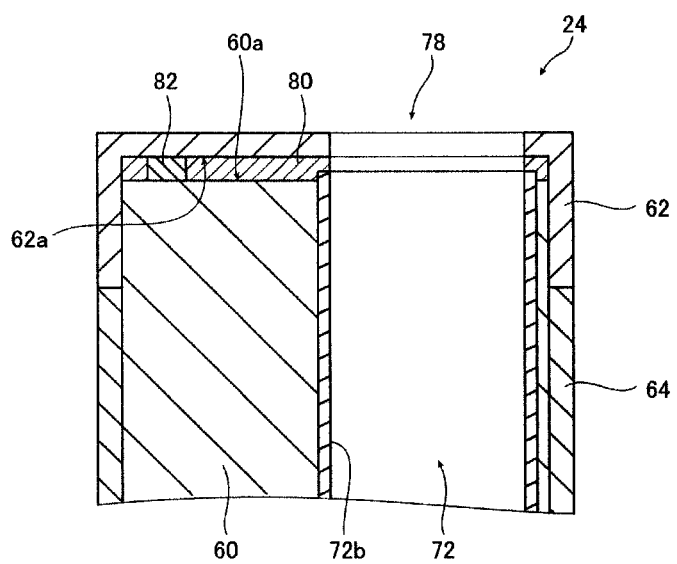
FIG. 4 is a diagram schematically showing a cross section of yet another example of the endoscopic insertion section tip of the present invention.

In a preferred embodiment shown in FIG. 4, a tube 72b forming a forceps hole 72 projects from a distal face 60a of a tip body 60 to such an extent that its projecting end portion is smaller in height than protrusions 82 (that is to say, a clearance is left between an opposite face 62a of a tip cap 62 and the distal end of the tube 72b).

In the case of an endoscopic insertion section tip with the configuration as shown in FIG. 4, an adhesive is applied to, for instance, the opposite face 62a of the tip cap 62 at a thickness exceeding the height of the protrusions 82, and the tip body 60 and the tip cap 62 are adhered together such that the adhesive overflows through the entire clearance between the tube 72b (namely, the forceps hole 72) and the opposite face 62a of the tip cap 62.

As is well-known, a liquid basically flows into a wider space. Consequently, the adhesive overflows through a narrow clearance between the tube 72b and the opposite face 62a after it runs through the region between the distal face 60a and the opposite face 62a that allows the adhesive to be distributed.

In other words, in the endoscopic insertion section tip of this embodiment, a region between parts of the distal face 60a and the opposite face 62a, which parts can be adhesion faces, is filled with the adhesive in its entirety, and the tip body 60 and the tip cap 62 are adhered together with a more reliable and higher sealing by causing the tube 72b forming the forceps hole 72 to project from the distal face 60a to such an extent that its projecting portion is smaller in height than the protrusions 82 and adhering the tip body 60 and the tip cap 62 to each other as described above.

No limitation is imposed on the difference in height between the projecting portion of the tube 72b and the protrusions 82, namely, the height of the clearance between the tube 72b and the opposite face 62a of the tip cap 62. The difference in height between the projecting portion of the tube 72b and the protrusions 82 may be specified at will as long as a clearance allowing the overflow of the adhesive is secured.

While the tube 72b forming the forceps hole 72 as shown in FIG. 4 projects from the distal face 60a, other configurations are also possible. In an exemplary configuration, a tube forming the forceps hole 72 may be similar to the tube 72a of FIG. 2, and the bumps which are smaller in height than the protrusions 82 and surround the forceps hole 72 in the same plane may be formed on the distal face 60a.

The endoscopic insertion section tip and the endoscope according to the present invention are as detailed above, although the present invention is in no way limited to the above embodiments. Various modifications and improvements may be made within the gist of the present invention.

What is claimed is:

1. A tip of an endoscopic insertion section to be inserted into a body cavity, comprising:
 a tip body having a forceps hole;
 a cap for covering a distal face of the tip body, the cap having an opening corresponding to the forceps hole;
 protrusions provided between the distal face of the tip body and a face of the cap that is opposite to the distal face; and
 an adhesive with which a gap formed by the protrusions between the distal face of the tip body and the face of the cap that is opposite to the distal face is filled,
 wherein the protrusions are equal in height,
 wherein the distal face of the tip body and the face of the cap that is opposite to the distal face are kept parallel to each other by the protrusions, and
 wherein the gap formed by the protrusions between the distal face of the tip body and the face of the cap that is opposite to the distal face is filled with the adhesive in its entirety; and
 wherein the distal face comprises a flat surface, the forceps hole is formed in the flat surface and the protrusions protrude from the flat surface.

2. The tip of an endoscopic insertion section according to claim 1, wherein the protrusions are three in total number.

3. The tip of an endoscopic insertion section according to claim 1, wherein the tip comprises one linear protrusion and another protrusion, with the protrusions being uniform in height of their tops.

4. The tip of an endoscopic insertion section according to claim 1, wherein the forceps hole has an extension throughout its perimeter that projects from the distal face of the tip body to such an extent that the extension is smaller in height than the protrusions.

5. The tip of an endoscopic insertion section according to claim 4, wherein the forceps hole includes a tubular member forming the forceps hole, and a distal end portion of the tubular member constitutes the extension.

6. The tip of an endoscopic insertion section according to claim 1, wherein the adhesive comprises an epoxy adhesive.

7. The tip of an endoscopic insertion section according to claim 1, wherein a height of the protrusions is in a range from 30 μm to 100 μm.

8. The tip of an endoscopic insertion section according to claim 1, wherein the protrusions comprise a first protrusion having a first shape, and a second protrusion having a second shape different from the first shape.

9. The tip of an endoscopic insertion section according to claim 1, wherein a sidewall of the opening in the cap is substantially aligned with a sidewall of the forceps hole, and
wherein a sidewall of the adhesive is substantially aligned with the sidewall of the opening in the cap and the sidewall of the forceps hole.

10. An endoscope comprising: an insertion section to be inserted into a body cavity, which is adapted to inspect a site to be inspected by inserting the insertion section into the body cavity,
a tip of the insertion section comprising:
a tip body having a forceps hole; a cap for covering a distal face of the tip body, the cap having an opening corresponding to the forceps hole;
protrusions provided between the distal face of the tip body and a face of the cap that is opposite to the distal face; and
an adhesive with which a gap formed by the protrusions between the distal face of the tip body and the face of the cap that is opposite to the distal face is filled,
wherein the protrusions of the tip of the insertion section are equal in height,
wherein the distal face of the tip body and the face of the cap that is opposite to the distal face are kept parallel to each other by the protrusions of the tip of the insertion section; and
wherein the gap formed by the protrusions of the tip of the insertion section between the distal face of the tip body and the face of the cap that is opposite to the distal face is filled with the adhesive in its entirety, and
wherein the distal face comprises a flat surface, the forceps hole is formed in the flat surface and the protrusions protrude from the flat surface.

11. The endoscope according to claim 10, wherein the protrusions of the tip are three in total number.

12. The endoscope according to claim 10, wherein the tip of the insertion section comprises one linear protrusion and another protrusion, with the protrusions being uniform in height of their tops.

13. The endoscope according to claim 10, wherein the forceps hole of the tip body has an extension throughout its perimeter that projects from the distal face of the tip body to such an extent that the extension is smaller in height than the protrusions.

14. The endoscope according to claim 13, wherein the forceps hole of the tip body includes a tubular member forming the forceps hole, and a distal end portion of the tubular member constitutes the extension.

15. A tip of an insertion section of an endoscope, the tip comprising:
a tip body;
a cap for covering a distal face of the tip body; protrusions a protrusion formed on at least one of:
a distal face of the tip body; and
a face of the cap that is opposite to the distal face; and
an adhesive which fills an entirety of a gap formed by the protrusions protrusion between the distal face of the tip body and the face of the cap that is opposite to the distal face wherein the protrusions are equal in height, and
wherein the distal face of the tip body and the face of the cap that is opposite to the distal face are kept parallel to each other by the protrusions; and
wherein the distal face comprises a flat surface, the forceps hole is formed in the flat surface and the protrusions protrude from the flat surface.

* * * * *